(12) United States Patent
Riel et al.

(10) Patent No.: US 11,000,880 B2
(45) Date of Patent: May 11, 2021

(54) MECHANICAL WAVEGUIDE PROVIDED WITH A MARKER THEREON

(71) Applicant: Les Solutions Medicales Soundbite Inc., Saint-Laurent (CA)

(72) Inventors: Louis-Philippe Riel, Montreal (CA); Steven Dion, Sherbrooke (CA); Martin Brouillette, Sherbrooke (CA); Wayne Cornish, Fallbrook, CA (US); Manuel Charlebois-Menard, Sherbrooke (CA)

(73) Assignee: Les Solutions Medicales Soundbite Inc., Saint-Laurent (CA)

( * ) Notice: Subject to any disclaimer, the term of this patent is extended or adjusted under 35 U.S.C. 154(b) by 71 days.

(21) Appl. No.: 16/096,212

(22) PCT Filed: Apr. 25, 2017

(86) PCT No.: PCT/IB2017/052387
§ 371 (c)(1),
(2) Date: Oct. 24, 2018

(87) PCT Pub. No.: WO2017/187347
PCT Pub. Date: Nov. 2, 2017

(65) Prior Publication Data
US 2019/0134668 A1    May 9, 2019

Related U.S. Application Data

(60) Provisional application No. 62/326,890, filed on Apr. 25, 2016, provisional application No. 62/424,014, filed on Nov. 18, 2016.

(51) Int. Cl.
*A61B 17/22* (2006.01)
*B06B 3/00* (2006.01)
(Continued)

(52) U.S. Cl.
CPC .............. *B06B 3/00* (2013.01); *A61B 6/12* (2013.01); *A61B 17/22012* (2013.01);
(Continued)

(58) Field of Classification Search
CPC ...... A61B 17/22012; A61B 17/320068; A61B 2017/320072; A61B 2017/22014; A61B 2017/22015; A61B 2090/3966
See application file for complete search history.

(56) References Cited

U.S. PATENT DOCUMENTS

| 5,304,115 A | * | 4/1994 | Pflueger | A61B 17/22012 |
| | | | | 604/22 |
| 5,382,228 A | | 1/1995 | Nita et al. | |

(Continued)

FOREIGN PATENT DOCUMENTS

| CA | 2251096 A1 | 8/1998 |
| CA | 2809746 A1 | 3/2012 |

(Continued)

OTHER PUBLICATIONS

International Search Report; Canadian Intellectual Property Office; International Application No. PCT/IB2017/052387; dated Aug. 2, 2017; 7 pages.

(Continued)

*Primary Examiner* — Alexander J Orkin
(74) *Attorney, Agent, or Firm* — Taft Stettinius & Hollister LLP (57) ABSTRACT

A device for transmitting mechanical waves, including a mechanical waveguide having an elongated shape and extending between a proximal end and a distal end for propagating the mechanical waves coupled at the proximal end up to the distal end, and a radiopaque marker secured to the mechanical waveguide adjacent to the distal end thereof.

23 Claims, 5 Drawing Sheets

(51) Int. Cl.
  *A61B 6/12* (2006.01)
  *G10K 11/24* (2006.01)
  *A61B 90/00* (2016.01)
  *A61B 17/32* (2006.01)
  *C22C 14/00* (2006.01)
  *A61B 17/00* (2006.01)

(52) U.S. Cl.
  CPC ...... *A61B 17/320068* (2013.01); *A61B 90/39* (2016.02); *C22C 14/00* (2013.01); *G10K 11/24* (2013.01); *A61B 2017/0084* (2013.01); *A61B 2017/00526* (2013.01); *A61B 2017/00938* (2013.01); *A61B 2017/00942* (2013.01); *A61B 2017/22014* (2013.01); *A61B 2017/22015* (2013.01); *A61B 2017/22018* (2013.01); *A61B 2017/22094* (2013.01); *A61B 2090/3966* (2016.02); *B06B 2201/76* (2013.01)

(56) References Cited

U.S. PATENT DOCUMENTS

| | | | | |
|---|---|---|---|---|
| 5,449,369 | A | * | 9/1995 | Imran ................ A61B 17/2202 600/585 |
| 5,824,042 | A | * | 10/1998 | Lombardi ................ A61F 2/07 623/1.13 |
| 6,730,048 | B1 | * | 5/2004 | Hare ................ A61B 17/22012 601/2 |
| 8,500,787 | B2 | | 8/2013 | Simpson et al. |
| 9,186,526 | B2 | * | 11/2015 | Akagane ........ A61B 17/320068 |
| 2003/0100848 | A1 | | 5/2003 | Goslengfiao et al. |
| 2005/0255317 | A1 | | 11/2005 | Bavaro et al. |
| 2013/0253387 | A1 | * | 9/2013 | Bonutti ................ A61B 17/24 601/46 |
| 2014/0107534 | A1 | | 4/2014 | Du et al. |
| 2016/0157884 | A1 | * | 6/2016 | Onuma ................ A61B 17/025 606/169 |

FOREIGN PATENT DOCUMENTS

EP 1985244 A2 10/2008
WO 2016170520 A1 10/2016

OTHER PUBLICATIONS

Written Opinion of the International Searching Authority; Canadian Intellectual Property Office; International Application No. PCT/IB2017/052387; dated Aug. 2, 2017; 8 pages.

* cited by examiner

MECHANICAL WAVEGUIDE PROVIDED WITH A MARKER THEREON

CROSS REFERENCE TO RELATED APPLICATIONS

This application is a U.S. National Phase of International PCT Application No. PCT/IB2017/052387 filed Apr. 25, 2017, which claims the benefit of U.S. Provisional Application No. 62/326,890 filed Apr. 25, 2016 and U.S. Provisional Application No. 62/424,014 filed Nov. 18, 2016, the contents of each application hereby incorporated by reference in their entirety.

TECHNICAL FIELD

The present invention relates to the field of mechanical waveguides, and more particularly to the field of mechanical waveguides for medical applications.

BACKGROUND

Minimally-invasive medical devices are attractive because they require a small incision to be made to the subject to be treated before insertion of the minimally-invasive medical device. Some minimally-invasive devices use a source of mechanical waves positioned outside the body of the subject and the mechanical waves are carried into the body to the lesion to be treated with a minimally-invasive device. To achieve this, the minimally-invasive device comprises a mechanical waveguide or transmission member to deliver the mechanical waves up to the lesion.

However, it would be beneficial for a user of the minimally-invasive device to be able to visualize the mechanical waveguide, and more particularly the distal end of the mechanical waveguide, while treating the lesion.

Therefore, there is a need for an improved mechanical waveguide to be used in a system for treating lesions.

SUMMARY

In accordance with a first broad aspect, there is provided a device for transmitting mechanical waves, comprising: a mechanical waveguide having an elongated shape and extending between a proximal end and a distal end for propagating the mechanical waves coupled at the proximal end up to the distal end; and a radiopaque marker secured to the mechanical wave adjacent to the distal end thereof.

In one embodiment, the mechanical waveguide comprising a recessed section adjacent to the distal end and the radiopaque marker is positioned over at least a portion of the recessed section.

In one embodiment, the radiopaque marker comprises a recess receiving aperture extending therealong, the recessed section extending at least partially within the recess receiving aperture of the radiopaque marker.

In one embodiment, the mechanical waveguide comprises a proximal section and a distal section each adjacent to the recessed section, the distal section comprising the distal end of the mechanical waveguide.

In one embodiment, the radiopaque marker extends between a first end and a second end, the first end abutting against one of the distal and proximal sections.

In one embodiment, the second end abuts against another one of the distal and proximal sections.

In one embodiment, the mechanical waveguide has a cylindrical shape.

In one embodiment, the distal section comprises a first distal portion adjacent to the recessed section and having an increasing diameter, and a second distal portion having a constant diameter and extending up to the distal end of the elongated member, the second end of the radiopaque marker abutting against the first distal portion of the distal section.

In one embodiment, the proximal section comprises a first proximal portion adjacent to the recessed section and having a decreasing diameter, and a second proximal portion having a substantially constant diameter, the first end of the radiopaque marker abutting against the first proximal portion of the proximal section.

In one embodiment, the proximal section further comprises a third proximal portion having an increasing diameter, the second proximal portion being located between the first and third proximal portions.

In one embodiment, the radiopaque marker comprises a coil wound around the recessed section.

In one embodiment, an internal diameter of the coil is substantially equal to a diameter of the recessed section of the mechanical waveguide.

In one embodiment, an internal diameter of the coil is greater than a diameter of the recessed section of the mechanical waveguide and less than a maximal diameter of the proximal and distal sections.

In one embodiment, the coil comprises a plurality of loops, at least one of a distal end of the coil and a proximal end of the coil being secured to an adjacent one of the plurality of loops.

In one embodiment, the coil comprises a plurality of loops and at least two adjacent ones of the plurality of loops being secured together.

In one embodiment, the coil is a single layer coil.

In another embodiment, the coil is a multi-layer coil.

In one embodiment, the radiopaque marker is one of made of and coated with one of tungsten, platinum, gold, a gold alloy and a doped polymer.

In one embodiment, wherein the mechanical waveguide is made of one of stainless steel, aluminum, aluminum alloy, titanium, titanium alloy, nitinol and fused quartz.

In one embodiment, the titanium alloy comprises one of Ti-6Al-4V and Ti-11.5Mo-6Zr-4.5Sn (Beta III titanium).

In one embodiment, at least a portion of the elongated member is coated with one of a hydrophilic coating and a hydrophobic coating.

In one embodiment, at least a portion of the elongated member is coated with polytetrafluoroethylene.

According to a second broad aspect, there is provided an assembly comprising: a mechanical waveguide comprising a first elongated structure extending along a first longitudinal axis between a proximal end and a distal end and provided with at least two protrusions projecting from an outer face of thereof adjacent to the distal end, the two protrusions being spaced apart by a given distance along the first longitudinal axis; and a radiopaque marker comprising a second elongated structure made of a radiopaque material and extending along a second longitudinal axis, the second elongated structure being hollow so as to be positioned around the first elongated structure between the two protrusions and being deformable so that an inner dimension thereof be reduced to maintain the second elongated structure between the two protrusions, wherein the inner dimension of the radiopaque marker is greater than an outer dimension of a section of the first elongated structure comprised between the two protrusions once deformed and positioned between the two protrusions.

In one embodiment, the first and second elongated structures have substantially a same cross-sectional shape.

In one embodiment, the first and second elongated structures have different cross-sectional shapes.

In one embodiment, the first elongated structure has a cylindrical shape and the second elongated structure has a tubular structure, an inner diameter of the second elongated structure being less than a transversal dimension of at least one of the two protrusions.

In one embodiment, the two protrusions extend along a portion of a circumference of the first elongated structure.

In one embodiment, at least one of the two protrusions extends along a whole circumference of the first elongated structure.

In one embodiment, the two protrusions are aligned along the longitudinal axis.

In one embodiment, the two protrusions each have one of a trapezoidal, hemi-spherical, cubic, and pyramidal shape.

In one embodiment, the second elongated structure is made of one of gold and platinum.

In one embodiment, the second elongated structure comprises a slot extending longitudinally from a proximal end thereof to a distal end thereof.

In one embodiment, the assembly further comprises a tube insertable around the radiopaque marker.

In one embodiment, the tube is made of a heat-shrinkable material.

According to another broad aspect, there is provided a method for making a mechanical waveguide structure; the method comprising: providing a mechanical waveguide comprising a first elongated structure, extending along a first longitudinal axis and provided with at least two protrusions projecting from an outer face of thereof, the two protrusions being spaced apart by a given distance along the longitudinal axis; providing a radiopaque marker comprising a second elongated structure made of a radiopaque material, extending along a second longitudinal axis and having a length being one of less than and equal to the given distance, the second elongated structure being hollow so as to be positioned around the first elongated structure between the two protrusions and being deformable so that an inner dimension thereof be reduced to maintain the second elongated structure between the two protrusions; positioning the second elongated structure around the first elongated structure between the two protrusions; and mechanically deforming the second elongated structure so that the inner dimension thereof be less than a transversal dimension of the two protrusions, thereby securing the radiopaque marker to the first elongated structure between the two protrusions, wherein the inner dimension of the radiopaque marker after said mechanically deforming is greater than an outer dimension of a section of the first elongated structure comprised between the two protrusions.

In one embodiment, the first and second elongated structures have substantially a same cross-sectional shape.

In one embodiment, the first and second elongated structures have different cross-sectional shapes.

In one embodiment, the first elongated structure has a cylindrical shape and the second elongated structure has a tubular structure, an inner diameter of the second elongated structure being less than a transversal dimension of at least one of the two protrusions.

In one embodiment, the two protrusions extend along a portion of a circumference of the first elongated structure.

In one embodiment, at least one of the two protrusions extends along a whole circumference of the first elongated structure.

In one embodiment, the two protrusions are aligned along the longitudinal axis

In one embodiment, the two protrusions each have one of a hemi-spherical, cubic, and pyramidal shape.

In one embodiment, the radiopaque marker is made of one of gold and platinum.

In one embodiment, said mechanically deforming comprises one of crimping and swaging the second elongated structure.

In one embodiment, the second elongated structure comprises a slot extending longitudinally from a proximal end thereof to a distal end thereof.

In one embodiment, said mechanically deforming comprises reducing a width of the slot.

In one embodiment, said reducing the width of the slot is performed until opposite sides of the slot abut each other.

In one embodiment, the method further comprises securing together the opposite sides of the slot.

In one embodiment, the method further comprises positioning a retaining tube over the radiopaque marker.

In one embodiment, the retaining tube is made of a heat-shrinkable material and further comprising heating the retaining tube.

For the purpose of the present description, a mechanical wave should be understood as a signal having arbitrary amplitude, duration, waveform, frequency, and/or the like. For example, a mechanical wave may have a high/low amplitude, a short/long duration, different waveforms, and any frequency content.

For the purpose of the present description, a mechanical pulse should be understood as a short duration mechanical wave. The duration of a mechanical pulse is of the order of 1/fc, where fc is the central frequency of the mechanical pulse, which is typically around 500 kHz, and typically within the range of 100 kHz to 1 MHz or more generally from 20 kHz to 5 MHz.

Furthermore, a mechanical waveguide should be understood as a waveguide adapted to propagate mechanical waves or pulses along its length. In the present description, the expressions "waveguide", "mechanical waveguide" and "transmission member" may be used interchangeably. The characteristics such as the shape, the dimensions, the material of which it is made, and/or the like may vary as long as mechanical waves and pulses may propagate along the mechanical waveguide. For example, a mechanical waveguide may have a cylindrical shape. The diameter of the mechanical waveguide may be constant along its length. Alternatively, the diameter of the waveguide may vary along its length so as to correspond to a taper or reverse profile for example. In an example, a mechanical waveguide may be a dispersive waveguide, whereby the speed of propagation of the mechanical waves depends on the modes of propagation and their frequency content. Alternatively, a mechanical waveguide may be non-dispersive.

The expression "radiopaque marker" refers to a body or device that is opaque to radiations used for imaging a subject, i.e., that prevents at least partially the propagation of the radiations therethrough. Therefore, while imaging a subject using adequate radiations, the radiopaque marker is visible on the images. Several different medical imaging techniques may be used for imaging a subject, such as radiography, magnetic resonance imaging, ultrasound imaging, tomography, etc. It should be understood that at least some of the characteristics of the radiopaque marker such as the material from which it is made are chosen as a function of the chosen medical imaging technique so that the radiopaque marker be visible on the images of the subject taken using the chosen medical imaging technique.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

In the following, there is described a mechanical waveguide or transmission member that comprises an elongated body extending between a proximal end and a distal end. The mechanical waveguide further comprises a radiopaque body secured to the elongated body at a position adjacent to the distal end of the elongated body.

Figure 1:
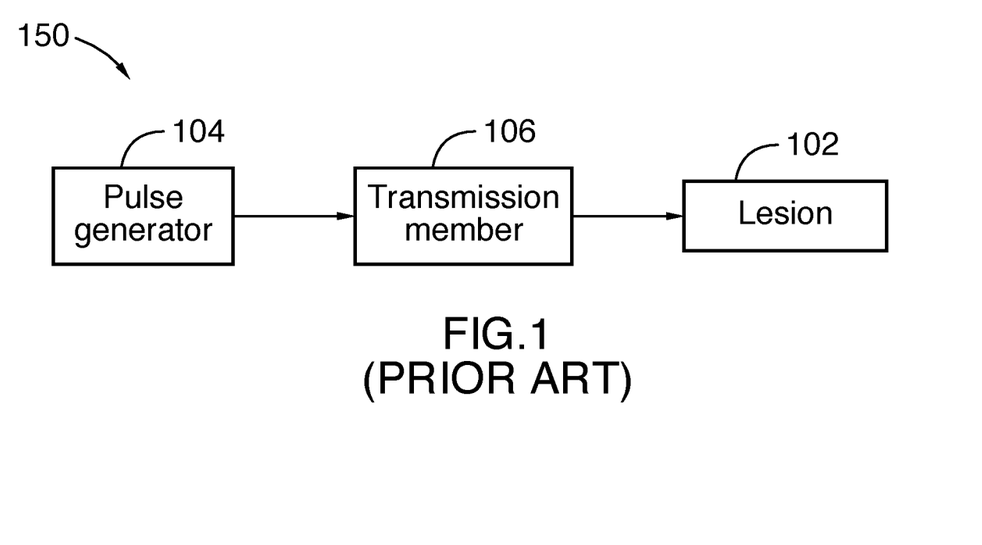
FIG. 1 is a block diagram illustrating a system for treating a lesion located in a blood vessel, in accordance with the prior art.

FIG. 1 illustrates an exemplary system 100 for treating a lesion 102 in order to order to describe an exemplary context in which the present mechanical waveguide provided with a radiopaque marker may be used. The system 100 comprises a pulse generator 104 for generating mechanical waves or pulses and a transmission member 106 for propagate the mechanical waves or pulses generated by the pulse generator 104 up to the lesion 102.

In one embodiment, the pulse generator 104 is adapted to generate a high amplitude and short duration pulse. The pulse generator 104 may comprise at least one broadband source and/or at least one narrow band source. The narrow or broad band source may be an electromechanical transducer. The pulse generator 104 may comprise a spatial concentrator to focus the output of at least one source toward a focal zone at which the proximal end of the transmission member 106 is located so as to couple the generated pulse therein.

The transmission member 106 such the present mechanical waveguide extends between a first or proximal end that is operatively connected to the pulse generator 104 and a second or distal end. The transmission member 106 is adapted to receive a mechanical pulse or wave at its proximal end and propagate the mechanical pulse up to its distal end. When it reaches the distal end, the mechanical pulse is at least partially transmitted to its surrounding medium to generate a transmitted pulse that propagates outside of the transmission member 106. It should be understood that part of the pulse may also be reflected by the distal end and propagates back in the transmission member 106 towards the proximal end thereof. The transmitted mechanical pulse corresponds to a mechanical pulse that propagates in the medium surrounding the distal end of the transmission member 106 up to the lesion 102. The transmitted pulse further propagates into the lesion 102, which may create cracks within the lesion 102, and eventually cleaves or breaks the lesion 102 into pieces.

In an embodiment in which the distal end of the transmission member 106 abuts against the lesion 102, the transmission member 106 may further be used to break the lesion 102 and/or drill a hole into the lesion 102. The transmission of the mechanical pulse at the distal end of the transmission member 106 creates a movement of the distal end of the transmission member 106. This movement may be along the longitudinal axis of the transmission member 106. Alternatively, the movement may be perpendicular to the longitudinal axis or it may be a combination of movements both along the longitudinal axis and perpendicular to the longitudinal axis of the transmission member. During this movement, the distal end of the transmission member 106 nominally first moves towards the lesion 102 and then moves back into its initial position. It should be understood that the movement may be inversed (i.e., thedistal end may first move away from the lesion 102 and then towards the lesion 102) depending on the polarity of the mechanical pulse reaching the distal end of the transmission member 106. When a plurality of distinct mechanical pulses are successively transmitted at the distal end of the transmission member 106, the movement of the distal end may be seen as a jack-hammer movement which may be used to treat the lesion 102.

In order to visualize the lesion 102 during a medical procedure, medical imaging is usually used. The transmission member comprises a radiopaque marker, as described below, that is secured adjacent to the distal end of a mechanical waveguide in order to localize the distal end of the mechanical waveguide relative to the lesion 2 to be treated on the X-ray images.

In one embodiment, the mechanical waveguide or transmission member provided with a radiopaque marker may be used to treat vascular occlusions, i.e., to cross an occlusion present in a blood vessel. In this case, at least a section of the transmission member is positioned within a blood vessel of a subject so that its distal end be adjacent to the occlusion. For example, the distal end of the transmission member may be in physical contact with the occlusion. When a mechanical pulse reaches the distal end of the transmission member, the distal end will impact onto the occlusion and transmits the mechanical pulse in the occlusion itself. If the distal end of the transmission member is not in physical contact with the occlusion, the mechanical pulse is transmitted in the medium present between the occlusion and the distal end, e.g. blood, saline fluid, contrast fluid or the like, and the transmitted mechanical pulse can propagate up to the occlusion. The mechanical pulse allows cracking, eroding cleaving, tunneling and/or breaking the occlusion and further allows the distal end of the transmission member to cross the occlusion as the distal end is moved farther within the vessel.

Figure 2:
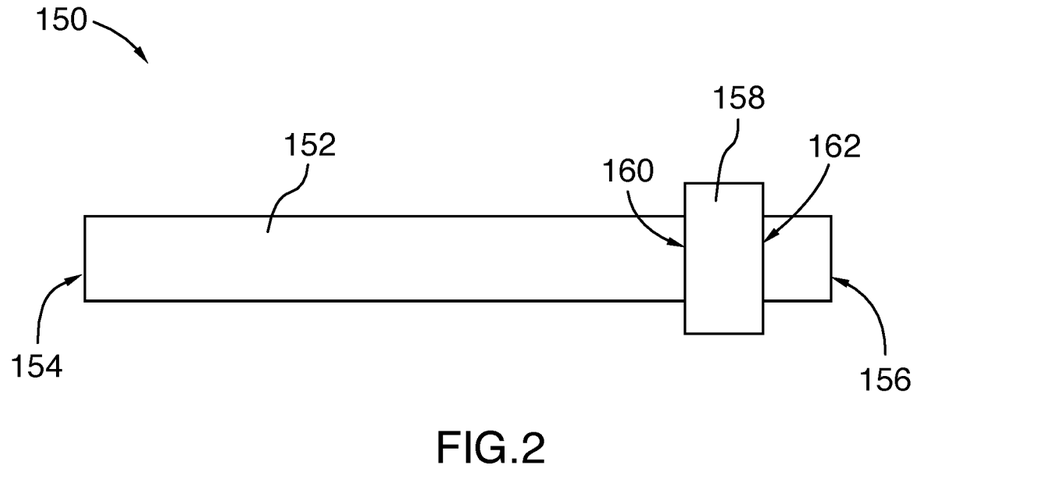
FIG. 2 is a block diagram illustrating a cylindrical mechanical waveguide having a constant diameter thereal-ong and having a radiopaque marker secured thereto, in accordance with an embodiment.

FIG. 2 illustrates one embodiment of a mechanical waveguide assembly 150 comprising a mechanical waveguide 152 in the shape of an elongated body that is made of a material adapted to propagate mechanical waves and/or pulses. The mechanical waveguide 152 extends longitudinally between a proximal end 154 and a distal end 156 and has a cylindrical shape. The distal end 154 of the mechanical waveguide 152 is adapted to receive mechanical waves or pulses which are then propagated along the mechanical waveguide 152 up to the distal end 156 thereof. In the illustrated embodiment, the diameter of the mechanical waveguide 152 is constant along a length thereof between the proximal and distal ends 154 and 156.

The mechanical waveguide assembly 150 further comprises a radiopaque marker 158 which has a tubular or annular shape and is mounted on the mechanical waveguide 152 adjacent to the distal end 156 thereof. The radiopaque marker 158 extends longitudinally between a proximal end 160 which faces the proximal end 154 of the mechanical waveguide 152 and a distal end 162 which faces the distal end 156 of the mechanical waveguide 152.

The radiopaque marker 158 allows locating the distal end 156 of the mechanical waveguide 152 while the mechanical waveguide 152 is inserted into the subject and images of the subject are taken. Such a marker allows visualizing the distal end 156 of the mechanical waveguide 152 with respect to an occlusion for example. Since the position of the marker 158 is known relative to that of the distal end 156 of the mechanical waveguide 152, visualizing the marker 158 allows a user to know or determine the position of the distal end 156 of the mechanical waveguide 152.

For example, when X-rays are used for imaging a subject, the marker 158 is chosen so as to be visible on X-ray images by preventing or limiting the propagation of the X-rays therethrough. In this case, the maker 158 may be made of or coated with a dense material such as tungsten, platinum, gold, gold alloys, doped polymer, or the like.

It should be understood that any adequate methods for securing the radiopaque marker 158 to the mechanical waveguide 152 may be used. For example, adhesive may be used. In another example, the radiopaque marker 158 may be welded to the mechanical waveguide 152. In a further example and as described below, protrusions projecting from the mechanical waveguide 152 or a recess formed into the mechanical waveguide 152 may be used to retain the radiopaque marker secured to the mechanical waveguide 152.

In one embodiment, the mechanical waveguide 152 may be made of a material adapted to minimize damping of mechanical waves such as stainless steel, aluminum or aluminum alloys, titanium or titanium alloys such as, Ti-6Al-4V or, Ti-11.5Mo-6Zr-4.5Sn (Beta III titanium), nitinol, fused quartz or the like. In one embodiment, a heat treatment such as annealing may be applied to at least a portion of the mechanical waveguide 152.

While it extends along the whole circumference of the mechanical waveguide 152, the radiopaque marker 158 may extend along only a section of the circumference of the mechanical waveguide 152. The radiopaque marker 158 may be fixedly secured to the mechanical waveguide 152. Alternatively, the radiopaque marker 158 may be movably secured to the mechanical waveguide 152. For example, the radiopaque marker 158 may have a single degree of freedom. For example, when secured to the mechanical waveguide 152, the radiopaque marker 158 may rotate around the mechanical waveguide 152 about the longitudinal axis thereof while being preventing from any other movements such as translating along the longitudinal axis of the mechanical waveguide 152 or translating along the transverse axis, i.e., the axis orthogonal to the longitudinal axis.

While in the illustrated embodiment, the distal end 162 of the radiopaque marker 158 is located at a given distance from the distal end 156 of the mechanical waveguide 152, it should be understood that the distal end 162 of the radiopaque marker 158 and the distal end 156 of the mechanical waveguide 152 may be coplanar.

While in the illustrated embodiment the internal diameter of the radiopaque marker 158 substantially corresponds to the external diameter of the mechanical waveguide 152, it should be understood that the internal diameter of the radiopaque marker 158 may be greater than the external diameter of the mechanical waveguide. In this case, screws may be used for securing the radiopaque marker 158 to the mechanical waveguide 152 for example.

As described below, the shape, size and position of the radiopaque marker 158 may vary as long as it may be secured to the mechanical waveguide 152 adjacent to the distal end 156 thereof.

While the mechanical waveguide 152 has a constant diameter along a length thereof, it should be understood that other configurations are possible. For example, the mechanical waveguide may comprise a recessed section along which the mechanical waveguide has a diameter that is less than that of the two sections that are adjacent to the recessed section. The radiopaque marker may be mounted over the recessed section of the mechanical waveguide. In another example, the mechanical waveguide may comprise at least two bumps or protrusions spaced apart by a given distance, i.e., a proximal protrusion and a distal protrusion. The section of the mechanical waveguide comprised between the two protrusions may be seen as a recessed section relative to the two protrusions, i.e., the diameter of the section comprised between the two protrusions is less than the maximal diameter of each protrusion while being may be equal to, greater than or less than the diameter of the remaining mechanical waveguide, i.e., the section of the mechanical waveguide which is proximal to the proximal protrusion and the section of the mechanical waveguide that is distal to the distal protrusion, if any. In an example in which the mechanical waveguide comprises a recessed section, the diameter of the recessed section may be constant therealong. In another example, the diameter of the recessed section may vary therealong.

While the mechanical waveguide 152 has a circular cross-section, it should be understood that the cross-section of the mechanical waveguide may have any other adequate shape such as oval, square, rectangular, etc. In this case, the transverse dimensions of the mechanical waveguide, i.e., the dimensions of the mechanical waveguide in a direction orthogonal to its longitudinal axis, may be constant over the length of the mechanical waveguide. In another example, the transverse dimensions of the mechanical waveguide may vary and the mechanical waveguide may comprise a recessed section adjacent to the distal end thereof. The marker is then positioned over the recessed section of the mechanical waveguide. The recessed section extends longitudinally along a given length of the mechanical waveguide and is comprised between a proximal section and a distal section of the mechanical waveguide. The distal section extends between the recessed section and the distal end of the mechanical waveguide. The proximal section is adjacent to the recessed section and extends from the recessed section towards the proximal end of the mechanical waveguide. The transverse dimensions of the recessed section are less than those of the proximal and distal sections, i.e., the surface area of the cross-section of the recessed section is less than that of the cross-section of the distal section and that of the cross-section of the proximal section so as to form a recess.

It should be understood that the maximal transverse dimensions of the proximal section are greater than the internal transverse dimensions of the proximal end of the marker so that the marker cannot pass over the proximal section. Similarly, the maximal transverse dimensions of the distal section are greater than the internal transverse dimensions of the distal end of the marker so that the marker cannot pass over the distal section.

In one embodiment, the surface area of the cross-section of the recessed section is constant along the recessed section. In another embodiment, the surface area of the cross-section of the recessed section may vary along the recessed section as long as the maximal cross-sectional surface area of the recessed section be less than the maximal cross-sectional surface area of the distal section and the maximal cross-sectional surface area of the proximal section.

Similarly, the cross-sectional surface area of the distal section and/or proximal section adjacent to the recessed section may vary therealong as long as the maximal cross-sectional surface area of the recessed section be less than the maximal cross-sectional surface area of the distal section and the maximal cross-sectional surface area of the proximal section. For example, a cylindrical proximal section may comprise three portions: a first or proximal portion having an increasing diameter, a second or distal section having a decreasing diameter and a third or middle portion having a constant diameter and comprised between the first and second portions.

Figure 3:
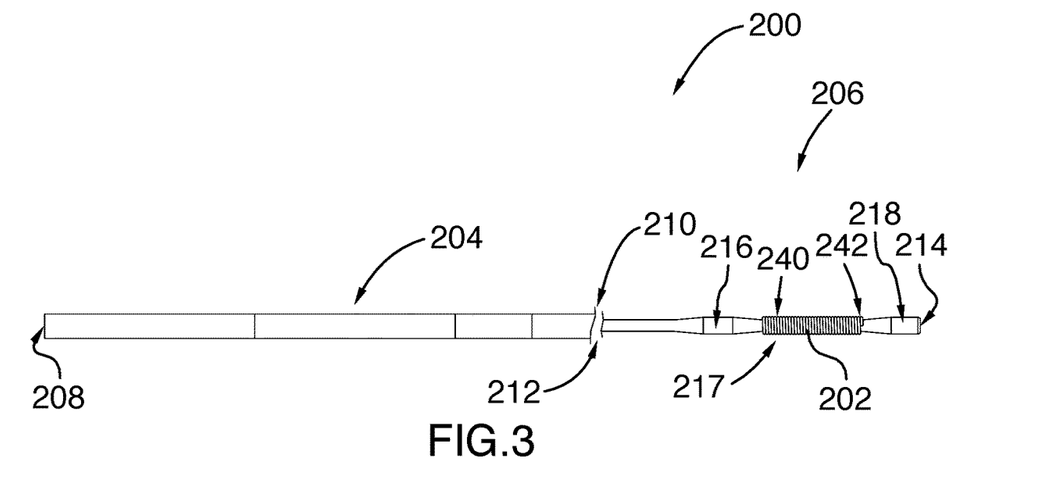
FIG. 3 illustrates a transmission member having a coil-shaped radiopaque marker secured thereon, in accordance with an embodiment.

FIG. 3 illustrates one embodiment of a cylindrical transmission member 200 provided with a coil shaped marker 202 having the shape of a single row or single layer coil. The transmission member 200 comprises a first section 204 and a second section 206 having a tapering transition in between. The diameter of the first section 204 is greater than that of the second section 206. The proximal end 208 of the first section 204 is connectable to a source of mechanical pulses to receive mechanical pulses therefrom and may have a shape different than the one illustrated in FIG. 3. The mechanical pulses propagate along the first section 204 from its proximal end 208 up to its distal end 214 before propagating in the tapering section. The proximal end 212 of the second section 206 receives the mechanical pulses from the tapering section and the mechanical pulses propagate up to the distal end 214 of the second section 206.

The second section 206 comprises a distal section 218 extending from the distal end 214 of the transmission member 200, a proximal section 216 and a recessed section 217 therebetween. The diameter of the recessed section 217 is less than that of the proximal and distal sections 216 and 218 so that the sections 216 and 218 appear as protrusions or bulbs relative to the recessed section 217. The sections 216 and 218 each protrude outwardly and radially from the transmission member 200 along the entire circumference of the transmission member 200.

Figure 4:
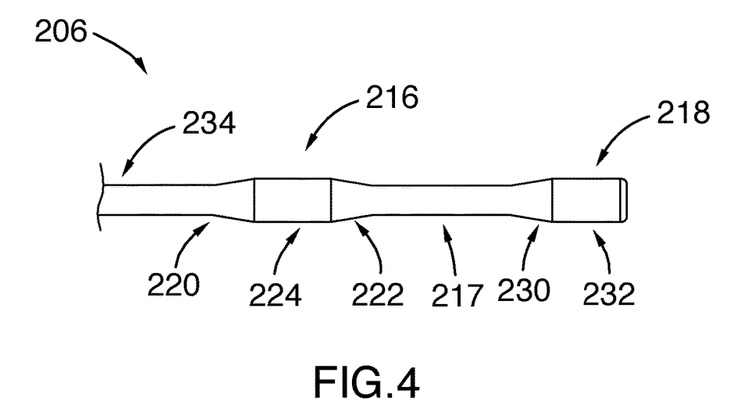
FIG. 4 illustrates a section of the transmission member of FIG. 3 adjacent to a distal end thereof with the coil-shaped radiopaque marker omitted, the section comprising a coil receiving portion located between two protrusions, in accordance with an embodiment.

As illustrated in FIG. 4, the proximal section 216 comprises three portions: a first or proximal portion 220, a second or distal portion 222 and a third or middle portion 224. The proximal portion 220 is a tapered portion having a diameter that increases therealong in direction of the recessed section 217. The middle portion 224 has a substantially constant diameter therealong. The distal portion 222 is a tapered portion having a diameter that decreases towards the recessed section 217.

The distal section 218 comprises two portions: a first or proximal portion 230 and a second or distal portion 232. The proximal portion 230 is a tapered portion having a diameter that increases therealong in direction of the distal end 214 and the distal portion 232 has a substantially constant diameter.

While in the illustrated embodiment it is substantially constant therealong, it should be understood that the diameter of the recessed section 217 could vary as long as the maximal diameter of the recessed section 217 is less than the maximal diameter of the proximal section 216 and the maximal diameter of the distal section 218.

As illustrated in FIG. 3, the coil shaped marker 202 is wound over the recessed section 206 between the proximal and distal sections 216 and 218. The marker 202 extends between a proximal end 240 and a distal end 242. The length and internal diameter of the marker 202 are chosen so that, when positioned over the recessed section 217, the proximal end 240 of the marker 202 abuts against the proximal section 216, i.e., against the wall of the tapered portion 222, and the distal end 242 abuts against the distal section 218, i.e., against the wall of the tapered portion 230. As a result of the abutment of the ends 240 and 242 of the marker 202 against the tapered portions 222 and 230, the coil shaped marker 202 is secured to the transmission member 200 and has a fixed position relative to the transmission member 200, i.e., the marker 202 cannot translate along the transmission member 200 once secured thereto. It should be understood that the marker 202 may rotate relative to the transmission member 200 about the longitudinal axis of the transmission 200 once secured thereto.

In one embodiment, the internal diameter of the coil-shaped marker 202 is substantially equal to that of the recessed section 206. In another embodiment, the internal diameter of the coil-shaped marker 202 is greater than that of the recessed section 206 while being less than the maximal diameter of the proximal and distal sections 216 and 218 so that the coil-shaped marker 202 be retained between the proximal and distal sections 216 and 218 while being rotatable relative to the transmission member 200.

In one embodiment, the length and the internal diameter of the marker 202 are chosen so that the coil-shaped marker 202 be movably secured to the transmission member 200, i.e., the coil-shaped marker 202 may translate along the transmission member 200 between the proximal and distal sections 216 and 218 and rotate about the longitudinal axis of the transmission member 200. For example, if it has a length equal to or less than that of the recessed section 217 and an internal diameter greater than that of the recessed section 217, then the marker 202 may be movably secured to the transmission member and may translate along a section of the transmission member 200 between the proximal and distal sections 216 and 218.

While in the illustrated embodiment, the diameter of the central portion 224 of the proximal section 216 is equal to that of the portion 232 of the distal section 218, it should be understood that other configurations may be possible as long as the maximal internal diameter of the marker 202 is less than the maximal diameter of the proximal and distal sections 216 and 218. Similarly, while the diameter of the recessed section 217 is substantially equal to that of the section 234 of the transmission member 200 that is located between the proximal section 216 and the proximal end 212. For example, the diameter of the recessed section 217 could be less than that of the section 234. In another embodiment, the diameter of the recessed section 217 could be greater than that of the section 234 as long as it is less than the maximal diameter of the proximal and distal sections 216 and 218.

It should be understood that more than one marker may be positioned over the recessed section 217. For example, two markers may be positioned side-by-side along the length of the recessed section 217.

It should be understood that the transmission member 200 may comprise more than one recessed section in order to secure more than one coil shaped marker to the transmission member 200 at different locations along the distal section 206 of the transmission member. In one embodiment, the different recessed sections and the different markers may have different dimensions such as a different diameter and/or a different length.

In one embodiment, the coil-shaped marker 202 comprises a radiopaque wire that is coiled around and over at least a portion of the recessed section 206 comprised between the proximal and distal sections 216 and 218. The radiopaque wire may be made of radiopaque material or coated with a radiopaque material such as such as tungsten, platinum, gold, gold alloys, doped polymer, or the like.

Figure 5:
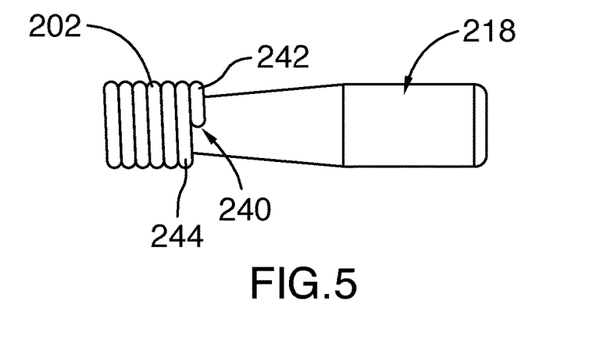
FIG. 5 illustrates a distal end of the transmission member of FIG. 3 having a coil-shaped radiopaque marker secured thereon.

In one embodiment, the coil-shaped marker 202 comprises a predefined number of loops which extend between a proximal loop adjacent to the proximal section 216 and a distal loop adjacent to the distal section 218. As illustrated in FIG. 5, the end 240 of the distal loop 242, i.e., the distal loose end 240 of the wire forming the coil 202, may be secured to the second-to-last loop 244 adjacent to the distal loop 242. For example, the loose end 240 of the distal loop 242 may be spot welded to the second-to-last loop 244. Similarly, the loose end of the proximal loop (i.e., the first loop) may be secured to the second loop. Securing the loose ends of the distal and proximal loops allows preventing any unwinding of the coil during use and smoothing the edges of the coil thereby protecting the vascular anatomy during the insertion of the transmission member 200 within the body of the subject. It should be understood that loops other than the proximal and distal loops may also be secured to neighbor loops It should be understood that the shape and dimensions of the proximal and distal sections 216 and 218 may vary as long as they allow maintaining the position of the marker 202 therebetween so as to secure the marker 202 to the transmission member 200. In the illustrated embodiment, the protrusion 216 comprises three portions: a proximal portion 220 having an increasing diameter, a distal portion 222 having a decreasing diameter, and an intermediary or central portion 224 located between the proximal and distal portion 220 and 222 and having a constant diameter. Within the proximal portion 220, the diameter of the proximal section 216 increases along a length thereof from the diameter of the section 234 of the transmission member 200 to the maximal diameter of the protrusion 216. The diameter of the central portion 224 is substantially constant along a length thereof and corresponds to the maximal diameter for the proximal section 216. Within the distal portion 222, the diameter of the protrusion 216 decreases along a length thereof from the maximal diameter of the protrusion 216 to the diameter of the recessed section 217. While the slope of the proximal and distal portions 220 and 222 is linear, it should be understood that other configurations may be possible. For example, the slope of the proximal and distal sections may be curved or may be sudden, i.e., a step.

In the illustrated embodiment, the distal section 218 comprises two portions: a proximal portion 230 having an increasing diameter and a distal portion 232 located between the recessed section 217 and the distal end 214 of the transmission member 200. Within the proximal portion 230, the diameter of the distal section 218 increases from the diameter of the recessed section 217 to the maximal diameter of the distal section 218. The diameter of the transmission member 200 within the distal portion 232 is substantially constant and corresponds to the maximal diameter for the distal section 218.

While in the illustrated embodiment, the proximal portion 220 of the proximal section 216 is substantially identical to the proximal portion 230 of the distal section 218 and the central portion 224 of the proximal section 216 is substantially identical to the central portion 232 of the distal section 218, it should be understood that other configurations may be possible. For example, the maximal diameter of the proximal section 216 may be greater or less than that of the distal section 218.

In one embodiment, the diameter of the section 204 of the transmission member 200 is substantially equal to 0.33 mm and the diameter of the recessed section 217 is substantially equal to 0.404 mm. The maximal diameter of the proximal and distal sections 216 and 218 is substantially equal to 0.432 mm. The length of the proximal, intermediary and distal portions 220, 224 and 222 of the proximal section 216 are each substantially equal to 0.5 mm. The length of the proximal and distal portions 230 and 232 of the distal section 218 are each substantially equal to 0.5 mm so that the distal end of the marker 202 is positioned at about 1 mm from the end 214 of the transmission member 200. The length of the marker 202 is substantially equal to 10 mm.

In one embodiment, the diameter of the section 204 of the transmission member 200 is substantially equal to 0.43 mm and the diameter of the recessed section 217 is substantially equal to 0.22 mm. The maximal diameter of the proximal and distal sections 216 and 218 is substantially equal to 0.28 mm. The length of the proximal, intermediary and distal portions 220, 224 and 222 of the proximal section 216 are each substantially equal to 0.5 mm. The length of the proximal and distal portions 230 and 232 of the distal section 218 are each substantially equal to 0.5 mm so that the distal end of the marker 202 is positioned at about 1 mm from the end 214 of the transmission member 200. The length of the marker 202 is substantially equal to 10 mm.

Figure 6:
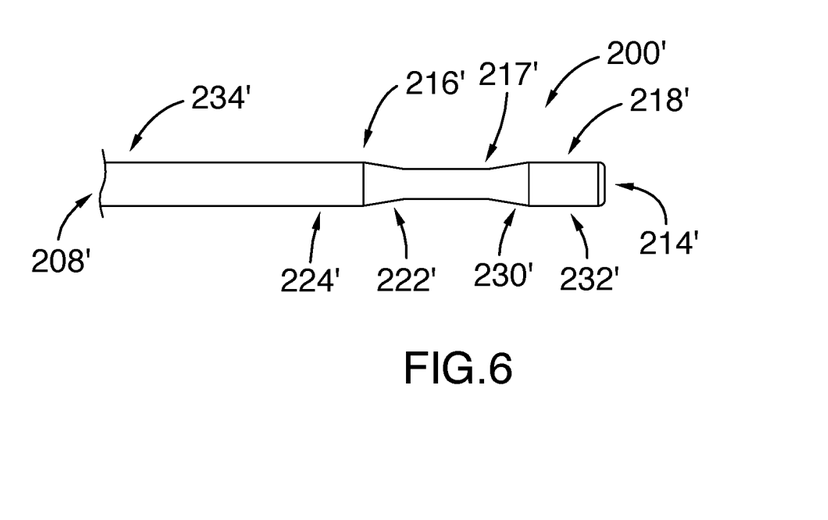
FIG. 6 illustrates a distal section of a transmission member provided with a recess for receiving a radiopaque marker thereon, in accordance with a first embodiment.

While in the illustrated embodiment, the proximal and distal sections 216 and 218 appear as protrusions relative to the section 234 of the transmission member, it should be understood that other configurations may be possible. For example, FIG. 6 illustrates one embodiment of a transmission member 200' comprising a recessed section 217'. The transmission member comprises a proximal section 216' which is adjacent to the recessed section 217' and located between the recessed section 217' and the proximal end 208' of the transmission member 200'. The transmission member also comprises a distal section 218' adjacent to the recessed section 217' and located between the recessed section 217' and the distal end 214' of the transmission member 200'. The transmission member 200' further comprises a section 234' which is located between the proximal section 216' and the proximal end 208'. In this embodiment, the proximal section 216' comprises no proximal portion such as proximal portion 220 and only comprises a constant diameter central portion 224' and a decreasing diameter distal portion 222'. The maximal diameter of the proximal section 216' corresponds to the diameter of the portion 224' which is identical to that of the section 234'. The distal section 218' comprises an increasing diameter proximal portion 230' and a constant diameter distal portion 232'. The maximal diameter of the proximal section 218' corresponds to the diameter of the distal portion 232' which is identical to that of the section 234'. As a result, the transmission member 200' appears as having a constant diameter along a length thereof except for the recessed section 217', the distal portion 222' of the proximal section 216' and the proximal portion 230' of the distal section 218' which all have a diameter that is less than that of the other sections of the transmission member 200'.

While the diameter of the distal portion 232' of the distal section 218' is equal to that of the portion 224' of the proximal section 216' and the section 234', it should be understood that other configurations may be possible. For example, the diameter of the distal portion 232' of the distal section 218' may be greater than that of the portion 224' of the proximal section 216' and the section 234'.

In one embodiment, the decreasing diameter section 222, 222' and the increasing diameter section 230, 230' allows reducing the propagation losses for the mechanical waves or pulses propagating along the transmission member 200, 200'.

Figure 7:
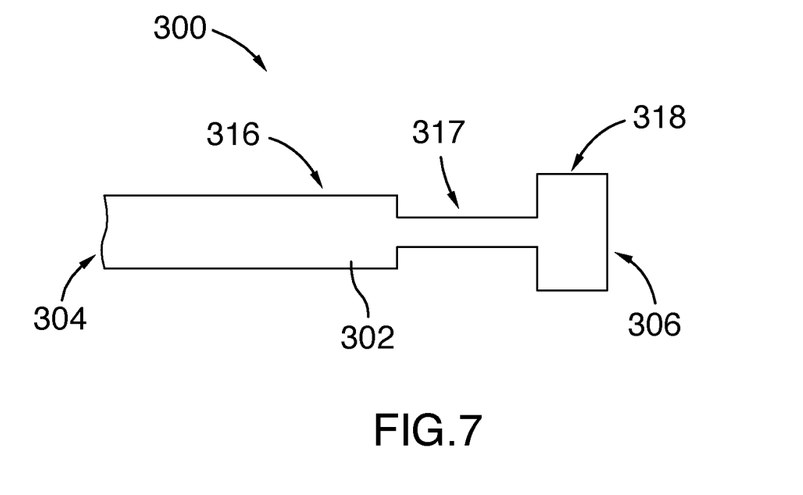
FIG. 7 illustrates a distal section of a transmission member provided with a recess for receiving a radiopaque marker thereon, in accordance with a second embodiment.

While FIGS. 4 and 6 illustrates a proximal section 216, 216' having a decreasing diameter section 222, 222' and a distal section 218, 218' having an increasing diameter section 230, 230', it should be understood that other configurations may be possible. For example, FIG. 7 illustrates a transmission member 300 comprising an elongated body 302 extending between a proximal end 304 and a distal end 306. The elongated body 302 comprises a recessed section 317 adjacent to the distal end 306, a proximal section 316 adjacent to the recessed section 317 and positioned between the recessed section 317 and the proximal end 304, and a distal section 318 adjacent to the recessed section 317 and located between the recessed section 317 and the distal end 306.

In this embodiment, the proximal section 316 comprises a single portion having a diameter that is greater than that of the recessed section 317 and greater than the internal diameter of the proximal end of the marker to be inserted over the recessed section 317. The distal section 318 comprises a single portion having a diameter that is also greater than that of the recessed section 317 and further greater than the internal diameter of the proximal end of the marker to be inserted over the recessed section 317. While the diameter of the distal section 318 is greater than that of the proximal section 316, it should be understood that other configurations may be possible.

In one embodiment, the transmission member 200 is made of Ti-11.5Mo-6Zr-4.5Sn (Beta III titanium) and at least a portion of the section 204 of the transmission member is coated with polytetrafluoroethylene (PTFE) while at least a portion of the section 206 of the transmission member 200 may be coated with a hydrophilic material or a hydrophobic material to allow improved movement through the anatomy and allow devices to easily slide over the transmission member 200. In one embodiment, the distal section 206 of the transmission member 200 may have no coating. It should be understood that the marker may also be coated with any adequate coating or combination of coatings.

While the recess 217 extends along the whole circumference of the transmission member 200, it should be understood that the recess 217 may extend along only a section of the circumference of the transmission member 200.

In one embodiment, the increased diameter of the distal section 218 provides at least two functions: providing an increased drilling diameter and maintaining the position of the marker 202.

While FIGS. 3-7 refer to a transmission member having a circular cross-section, it should be understood that other configurations may be possible. For example, the transmission member may consist in an elongated member extending between a proximal end and a distal end and having a square or rectangular cross-section.

While FIG. 3 refers to a marker 202 having a coil shape, it should be understood that other shape may be provided to the marker 202 as long as the marker consists in an elongated and hollow body mountable over the recessed section 217 and of which the distal and proximal ends of the internal cavity formed by the elongated and hollow body have transverse or cross-sectional dimensions that are less than those of the proximal and distal sections adjacent thereof. For example, the marker 202 may have a tubular shape and may surround the transmission member 200. In one embodiment, the tubular marker 202 may have an opening along a length thereof in order to position the tubular marker 202 around the transmission member 200. A tubular marker 202 may also be molded or screwed over the transmission member 200. In the case of a tubular marker comprises no opening, the tubular marker 202 may be inserted around the transmission member before the protrusion 218 be created. For example, the protrusion 218 may then be created using welding, forging, or the like.

In another example, the marker may consist in an elongated body defining an opening extending through the entire length thereof. The opening is sized and shaped for receiving at least a portion of the recessed section of the transmission member therein. The cross-section of the opening may have any adequate shape such as circular, square, rectangular, or the like as long as at least one transverse or cross-sectional dimension of the opening is less than the transverse dimension of the distal and proximal sections adjacent to the recessed section. For example, the transverse dimension of the opening may vary along the length of the marker as long as the transverse dimension of the distal and proximal ends of the opening is less than the transverse dimension of the distal and proximal sections, respectively.

In an embodiment in which the marker 202 has a coil shape, the contact surface area between the marker 202 and the transmission member 200 may be reduced with respect to a configuration in which the marker 202 has a tubular shape for example. As a result, the propagation losses of the mechanical pulses may be reduced when a coil-shaped marker 202 is used.

In another embodiment, the marker 202 may comprise a braided sleeve whose inner diameter decreases as the length of the sleeve is increased.

In an embodiment in which the marker 202 has a coil shape, the marker 202 may be fixedly secured to the transmission member 200 in order to improve its mechanical integrity. For example, adhesive, soldering, welding, or the like may be used for securing the coil shaped marker 202 to the transmission member 200.

In one embodiment, the transmission member 200 is made of an alloy that can transmit mechanical waves or pulses from the proximal end 208 to the distal end 214. The distal section 206 may be more flexible than the proximal section 204. The flexibility of the distal section 206 may be achieved through a reduction in diameter of the transmission member 200 and/or the selection of an appropriate material. The reduction in diameter can be achieved using a single taper or a series of tapers in order to obtain an increased flexibility for the distal section 206. The length and/or diameter of the proximal and distal sections 216 and 218 are chosen so that the proximal and distal sections 216 and 218 do not significantly decrease the flexibility of the distal section 206. In one embodiment, the flexibility of the distal section 206 may be increased only in one direction of its cross-section. This may be achieved via a reduction of dimension only in the direction of the cross-section of the distal section 206 for which the increase of flexibility is desired.

While the coil shaped marker 202 comprises a single row/layer, it should be understood that other configurations may be possible. For example, the marker 202 may comprise at least two rows or layers of coil made from a continuous wire and wound in alternating directions around the recess section 217. In this case, both loose ends of the coil are located at the same end of the marker 202 and they may be welded together to close the coil. In another example, the coil may be made of a continuous wire that is wound around the recessed section from a first end to a second and after making the last loop at the second end, the continuous wire may be inserted under the coil up to the first end where the two loose ends of the continuous wire are located. The two loose ends located at the first end of the coil may be secured together. In another example, the marker 202 may comprise a coil having different pitch angles along its length. In a further example, the coil may be made of a continuous wire that is wound around the recessed section of the mechanical waveguide from a first end to a second. After making the last loop at the second end, the continuous wire is coiled back, over the existing coil or within the existing coil, to the first end where the two loose ends of the continuous wire are located. The two loose ends located at the first end of the coil may then be secured together. In this case, a U-turn may be performed at the second end so that the wire is then wound around the mechanical waveguide from the second end to the first end.

As a mechanical wave or pulse propagates along the transmission member 200, some mechanical energy may leak out from the transmission member 200 into the surrounding medium. In one embodiment, the marker 202 located between the transmission member 200 and the surrounding medium may prevent or minimize mechanical energy to leak out into the surrounding medium.

In one embodiment, the material, size and shape of the marker 202 are chosen so that the marker 202 be flexible enough to allow shaping the distal tip of the transmission member.

Figure 8:
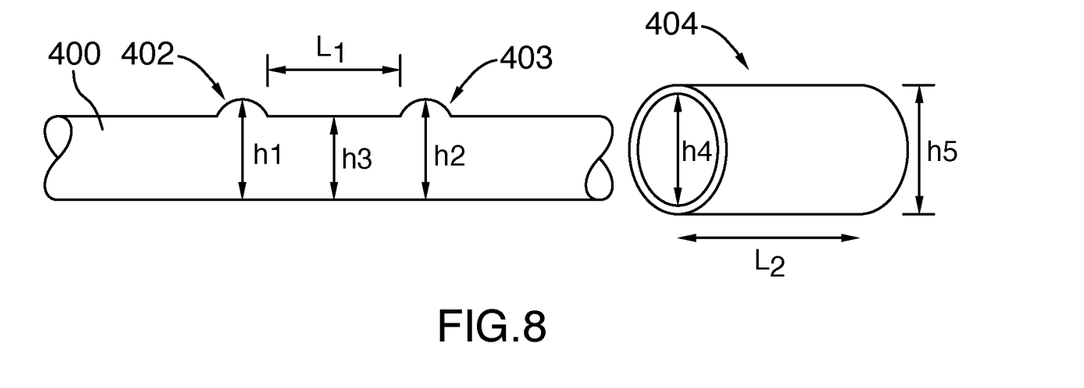
FIG. 8 illustrates an assembly formed of a mechanical waveguide and an independent radiopaque marker before securing the two together, in accordance with an embodiment.

While the above-described mechanical waveguides 200 and 300 comprises protrusions 216, 218 and 318 which extend along the whole circumference of the mechanical waveguide 200 and 330, other configurations may be possible as illustrated in FIG. 8.

Figure 9:
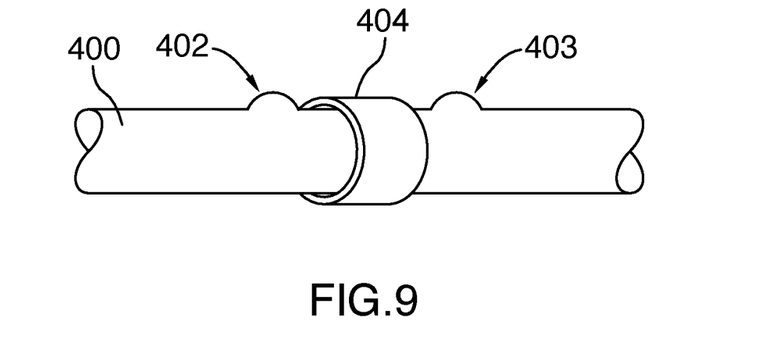
FIG. 9 illustrates the assembly of FIG. 8 when the radiopaque marker is secured to the mechanical waveguide.

FIG. 8 illustrates one embodiment of a mechanical waveguide assembly formed of a transmission member or mechanical waveguide 400 and a radiopaque marker 404. In FIG. 8, the radiopaque marker 404 is illustrated before being secured to the mechanical waveguide 400 and is therefore independent and separate from the mechanical waveguide 400. FIG. 9 illustrates the radiopaque marker 404 when secured to the mechanical waveguide 400.

The mechanical waveguide 400 has a cylindrical or tubular shape with a local outer transversal dimension h3, i.e., a local outer diameter h3 in this embodiment, and extends along a longitudinal axis between a proximal end and a distal end. When the mechanical waveguide 400 is used for propagating mechanical waves, at least a section of the mechanical waveguide 400 is adapted to be inserted into a subject such as into a blood vessel of the subject so that its distal end be positioned adjacent to a lesion to be treated in order to propagate the mechanical waves up to the lesion.

The outer surface of the mechanical waveguide 400 is provided with at least two protrusions or bumps 402 and 403 which project radially and outwardly therefrom. The two bumps 402 and 403 are spaced apart along the longitudinal axis by a distance L1. In the illustrated embodiment, the bumps 402 and 403 each have a hemi-spherical shape.

The transversal dimension of the first bump 402, i.e., the distance between the apex of the bump 400 and the opposite face of the mechanical waveguide 400 along the transverse axis orthogonal to the longitudinal axis, is defined as h1. Similarly, the transversal dimension of the second bump 403, i.e., the distance between the apex of the bump 402 and the opposite face of the mechanical waveguide 400 along the transverse axis orthogonal to the longitudinal axis, is defined as h2.

It should be understood that the location of the bumps 402 and 403 along the longitudinal axis of the mechanical waveguide 400 may vary. In one embodiment, the bump 403 is located adjacent to the distal end of the mechanical waveguide 400.

As described above, the assembly further comprises the radiopaque marker 404 which has a tubular shape. The radiopaque marker 404 extends linearly along a longitudinal axis. The radiopaque marker 404 is provided with an internal transversal dimension h4, i.e., an internal diameter h4 in the illustrated embodiment, an external transversal dimension h5, i.e., an external diameter h5 in the illustrated embodiment, and a length L2.

The internal or inner diameter h4 of the radiopaque marker is chosen to be greater than the transversal dimensions h1 and h2 of the first and second bumps 402 and 403, respectively, so that the mechanical waveguide 400 be inserted into the radiopaque marker 404. The length L2 of the radiopaque marker 404 is chosen to be less than the distance L1 between the two bumps 402 and 403.

The radiopaque marker 404 is made of a radiopaque material and the thickness and material of the radiopaque marker 404 are chosen so that the radiopaque marker 404 be ductile or deformable.

In order to secure the radiopaque marker 404 on the mechanical waveguide 400, the radiopaque marker 404 is inserted around the mechanical waveguide 400 and slid along the longitudinal axis of the mechanical waveguide 400 until it is located between the bumps 402 and 403. Once in place, the radiopaque marker 404 is mechanically deformed by crimping or swaging from its outer surface to reduce its inner dimension h4 to a value being less than the transversal dimensions h1 and h2. As a result, the deformed radiopaque marker 404 is secured to the mechanical waveguide 400 as illustrated in FIG. 9. Since the final inner dimension h4 of the radiopaque marker 404 is less than the transversal dimension h1 of the first bump 402, the radiopaque marker 404 cannot pass over the first bump 402. Similarly, the radiopaque marker 404 cannot pass over the second bump 403 since the final inner dimension h4 of the radiopaque marker 404 is less than the transversal dimension h2 of the second bump 403. As a result, the radiopaque marker 404 is maintained between the two bumps 402 and 403.

In one embodiment, the length L2 of the radiopaque marker 404 is chosen so that the proximal end of the radiopaque marker 404 abuts against the distal face of the first bump 402 and the distal end of the radiopaque marker 404 abuts against the proximal face of the second bump 403 when the radiopaque marker 404 is secured to the mechanical waveguide 400. In this case, the radiopaque marker 404 cannot slide or translate along the mechanical waveguide 400 once secured thereto between the two bumps 402 and 403.

In another embodiment, the length L2 of the radiopaque marker 404 is chosen so that the radiopaque marker 404 may slide between the two bumps 402 and 403 once secured to the mechanical waveguide 400, i.e., the radiopaque marker 404 does not abut against both bumps 402 and 403 once secured to the mechanical waveguide 400. In this case, contact between the mechanical waveguide 400 and radiopaque marker 404 is minimal, thus preventing mechanical energy leakage between the mechanical waveguide 400 and the radiopaque marker 404.

In one embodiment, the final inner dimension h4 of the radiopaque marker once secured to mechanical waveguide 400 is substantially equal to the diameter h3 of the mechanical waveguide 400 so that no transverse movement of the radiopaque marker 404 relative to the mechanical waveguide 400 be possible.

In another embodiment, the final inner dimension h4 of the radiopaque marker 404 is greater than the diameter h3 of the mechanical waveguide 400, thereby allowing a transverse movement of the radiopaque marker 404 relative to the mechanical waveguide 400. In this case, contact between the mechanical waveguide 400 and the radiopaque marker 404 is minimal, thus preventing mechanical energy leakage between the mechanical waveguide 400 and the radiopaque marker 404.

While in the illustrated embodiment the bumps 402 and 403 each have a hemi-spherical shape, it should be understood that any other adequate shape may be provided for the bumps. For example, the bumps 402 and 403 may have a trapezoidal, pyramidal or cubic shape. It should also be understood that the bumps 402 and 403 may be provided with different shapes.

While in the illustrated embodiment the bumps 402 and 403 are located at as same angular position along the circumference of the mechanical waveguide 400, it should be understood that other configurations are possible. For example, the bumps 402 and 403 may project from opposite sides of the mechanical waveguide 400.

While in the illustrated embodiment the bumps 402 and 403 each extend along a portion of the circumference of the mechanical waveguide 400, it should be understood that at least one bump 402, 403 may extend along the whole circumference of the mechanical waveguide 400, thereby forming a ring. In this case, the transversal dimension of the bump corresponds to the external diameter of the ring.

In one embodiment, the radiopaque marker 404 is made of a sufficiently radiopaque and ductile material in order to ensure good visibility on medical images and manufacturability. For example, the radiopaque marker 404 may be made of gold or platinum.

While in the illustrated embodiment, the mechanical waveguide 400 and the radiopaque marker 404 have a cylindrical or tubular shape, it should be understood that the mechanical waveguide 400 and the radiopaque marker 404 may have different geometries. For example, the mechanical waveguide 400 and the radiopaque marker may each have a substantially rectangular or square cross-sectional shape.

While in the illustrated embodiment the mechanical waveguide 400 and the marker 404 each have substantially the same shape, i.e., a cylindrical or tubular shape, it should be understood that other configurations may be possible. For example, the mechanical waveguide 400 may have a cylindrical shape while the radiopaque marker 404 may have a rectangular or square cross-sectional shape.

It should be understood that the shape and inner dimensions of the radiopaque marker 404 before securing to the mechanical waveguide 400 may vary as long as the radiopaque marker 404 may be inserted around the mechanical waveguide 400 and over at least one bump 402, 403 to be positioned between the bumps 402 and 403. For example, the inner dimension of the radiopaque marker 404 may be greater than the transversal dimension of the second bump 403 but less than the transversal dimension of the first bump 402. In this case, the radiopaque marker 404 is inserted around the mechanical waveguide 400 from the distal end thereof and slid over the second bump 403 to be positioned between the two bumps 402 and 403. In another example, the inner dimension of the radiopaque marker 404 may be greater than the transversal dimension of the first bump 402 but less than the transversal dimension of the second bump 403. In this case, the radiopaque marker 404 is inserted around the mechanical waveguide 400 from the proximal end thereof and slid over the first bump 402 to be positioned between the two bumps 402 and 403. In a further example, the inner dimension of the radiopaque marker 404 may be greater than the transversal dimension of both the first and second bumps 402 and 403 as described above.

It should also be understood that the radiopaque marker 404 once positioned between the two bumps may be deformed in any adequate manner as long as its final maximal inner dimension be less than the transversal dimension of the two bumps 402 and 403. In one embodiment, the final inner dimension of the radiopaque marker 404 is chosen so as to minimize contact between the deformed radiopaque marker 404 and the mechanical waveguide 400.

The generally tubular initial geometry of the radio-opaque marker can be full or segmented. For example the radiopaque marker 404 can comprise a plurality of distinct or joined rings of uniform or varying individual length, all of generally the same cross-sectional geometry. The marker can also comprise a wire wound as a coil, or comprise a combination of distinct or joined tubes, distinct or joined rings, and coils.

In one embodiment, once crimped or swaged, the radiopaque marker 404 can have a regular and smooth inner and/or outer surface, or it can have an irregular inner and/or outer surface, comprising features such as folds or ridges, for example. This irregular final surface can be encouraged by manufacturing the radiopaque marker 404 with pre-formed folds or ridges that, upon crimping or swaging, are amplified into larger folds, ridges or pleats, for example. This geometry may be useful to minimize contact between the radiopaque marker and the mechanical waveguide 400.

Figure 10:
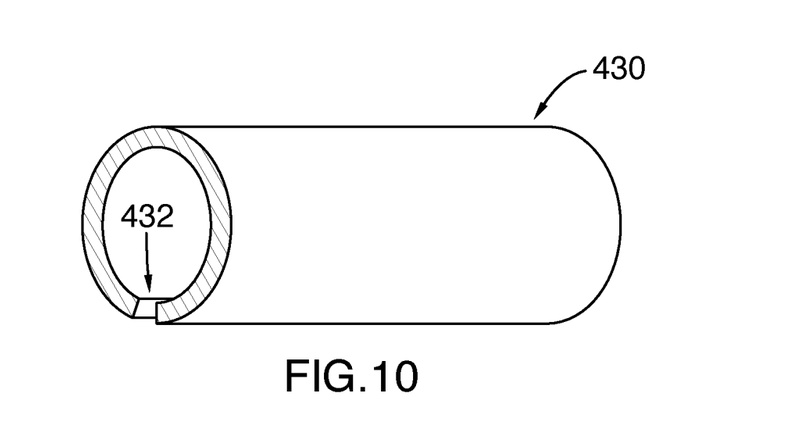
FIG. 10 illustrates a slotted tubular radiopaque marker, in accordance with an embodiment.

FIG. 10 illustrates an embodiment of a slotted radiopaque marker 430. Similarly to the radiopaque marker 404, the radiopaque marker 430 has a tubular shape and extends along a longitudinal axis. The radiopaque marker 430 also comprises a slot or aperture 432 that extends linearly along the longitudinal axis of the radiopaque marker 430 from the proximal end thereof to the distal end thereof. The width of the slot 432 is chosen so as to be greater than the lateral dimension of the mechanical waveguide 400, thereby allowing the radiopaque marker 430 to be slipped on the mechanical waveguide 400 from its side. Once positioned between the bumps 402 and 403, the slot 432 is closed by crimping or swaging to prevent the radiopaque marker 430 from slipping out from the side of the mechanical waveguide 400. The final geometry of the crimped or swaged radiopaque marker 430 is such that the radiopaque marker 430 is also prevented from axially slipping out from its location between the two bumps 402 and 403 on the mechanical waveguide 400, while physical contact is minimized between the radiopaque marker 430 and the mechanical waveguide 400.

In one embodiment, once this slotted tubular marker is in place over the mechanical waveguide 400, the slot 432 is partially closed so that the final width of the slot 432 is not wide enough to allow the radiopaque marker 432 slipping out from the side of the mechanical waveguide 400.

In another embodiment, the slot 432 is fully closed. The closed slot 432 may be achieved by having both sides of the slot 432 abutting each other or having both sides overlapping each other.

In order to prevent the slot 432 from re-opening, the open or closed slot 432 can be partially or fully joined by welding, brazing or gluing, for example. Another method to prevent the slot 432 from re-opening consists in covering the outer circumference of the radiopaque marker 430 with a retaining tube or sleeve of the same inside dimensions as that of the outer dimensions of the radiopaque marker 430. This retaining tube can be fixed in place by welding, brazing or gluing to the radiopaque marker 430, for example. The retaining tube can also be made of a heat-shrinking material, where heat application ensures that the retaining tube is securely attached to the radiopaque marker 430.

The radiopaque marker 430 can be full or segmented. For example the radiopaque marker 430 can comprise a plurality of distinct or joined slotted rings of uniform or varying individual length, all of generally the same cross-sectional geometry. The radiopaque marker 430 can also comprise a combination of distinct or joined slotted tubes and rings.

Figure 11:
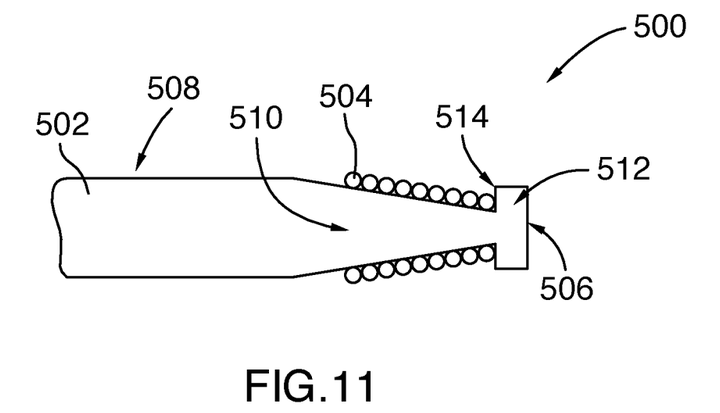
FIG. 11 illustrates a cylindrical mechanical waveguide having a diameter varying recess and a radiopaque marker secured thereto, in accordance with a first embodiment.
Figure 12:
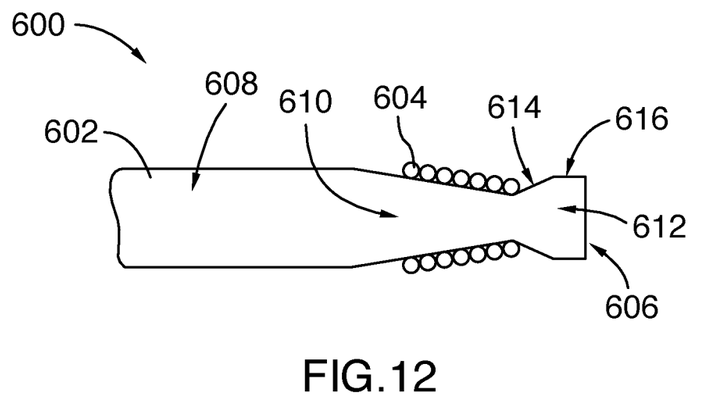
FIG. 12 illustrates a cylindrical mechanical waveguide having a diameter varying recess and a radiopaque marker secured thereto, in accordance with a second embodiment.

While in the above-described mechanical waveguides provided with a recess section, the recess section has constant transverse dimensions, e.g., a constant diameter along the length of the recessed section, it should be understood that the transverse dimensions of the recessed section may vary therealong as illustrated in FIGS. 11 and 12.

FIG. 11 illustrates one embodiment of a mechanical waveguide assembly 500 comprising a mechanical waveguide 502 and a coil-shaped radiopaque marker 504 secured to the mechanical waveguide 502. The mechanical waveguide 502 has a generally cylindrical shape, i.e., the cross-section of the mechanical waveguide 502 is circular. The mechanical waveguide 502 extends between a proximal end (not shown) and a distal end 506, and comprises a proximal section 508 a distal section 512 and a recessed section 510 located between the proximal and distal sections 508 and 512. The proximal section 508 has a constant diameter D1 along a length thereof and the distal section 512 has also a constant diameter D2 along a length thereof. The diameter D3 of the recessed section 510 decreases from a proximal end thereof to a distal end thereof. The diameter D3 of the recessed section 510 at the proximal end is equal to the diameter D1 of the proximal section 508 while the diameter D3 of the recessed section 510 at the distal end is less than the diameter D2 of the distal section 512. The diameter D2 of the distal section 512 may be equal to, less than or greater than the diameter D1 of the proximal section 508 as long as it is greater than the diameter D3 at the distal end of the recessed section 510.

The radiopaque marker 504 comprises a coil wound around the recessed section 510 and has a substantially tubular shape. The radiopaque marker 504 extends between a proximal end and a distal end and the length of the radiopaque marker 504 is less than the length of the recessed section 510. When the radiopaque marker 504 is secured to the mechanical waveguide 500 and for each point of the radiopaque marker 504 along the length thereof, the internal diameter of the radiopaque marker 504 is substantially equal to the diameter D3 of the recessed section The distal end of the radiopaque marker 504, i.e., the distal loop of the coil, abuts against the proximal wall 514 of the distal section 512. Since the length of the radiopaque marker 504 is less than that of the recessed section 510, the diameter of the radiopaque marker 504 at its proximal end is less than the diameter D1 of the proximal section 508.

Since the distal end of the radiopaque marker 504 abuts against the proximal wall 514 of the distal section 512 and the diameter of the proximal end of the radiopaque marker 504 is less than the maximal diameter of the recessed section 510, i.e., the diameter D1, the radiopaque marker 504 is secured to the mechanical waveguide 502 and cannot translate along the longitudinal axis of the mechanical waveguide 502. In one embodiment, the radiopaque marker 504 may rotate about the longitudinal axis of the mechanical waveguide 502 once secured thereto.

It should be understood that the dimensions of the radiopaque marker 504 may vary as long as its length is less than the length of the recessed section 510, its diameter at its proximal length is less than the maximal diameter of the recessed section, i.e., diameter D1, and its diameter at its distal end is less than the diameter D2 of the distal section 512. For example, for each point along the length of the radiopaque marker 504, the diameter of the radiopaque marker 504 may be greater than the diameter of the recessed section 510 as long as the diameter of the proximal end of the radiopaque marker 504 is less than D1 and the diameter of the distal end of the radiopaque marker 504 is less than D2.

FIG. 12 illustrates one embodiment of a mechanical waveguide assembly 600 comprising a mechanical waveguide 602 and a coil-shaped radiopaque marker 604 secured to the mechanical waveguide 602. The mechanical waveguide 602 has a generally cylindrical shape, i.e., the cross-section of the mechanical waveguide 602 is circular. The mechanical waveguide 602 extends between a proximal end (not shown) and a distal end 606, and comprises a proximal section 608 a distal section 612 and a recessed section 610 located between the proximal and distal sections 608 and 612. The proximal section 608 has a constant diameter D1 along a length thereof. The distal section 612 comprises a proximal portion 614 and a distal portion 616. The diameter of the proximal portion 614 increases from the recessed section 610 to the distal portion 616 and the distal portion 606 has a constant diameter D2 along a length thereof. The diameter D3 of the recessed section 610 decreases from a proximal end thereof to a distal end thereof. The diameter D3 of the recessed section 610 at the proximal end is equal to the diameter D1 of the proximal section 608 while the diameter D3 of the recessed section 610 at the distal end is less than the diameter D2 of the distal portion 616. The diameter D2 of the distal portion 616 may be equal to, less than or greater than the diameter D1 of the proximal section 608 as long as it is greater than the diameter D3 at the distal end of the recessed section 610.

The radiopaque marker 604 comprises a coil wound around the recessed section 610 and has a substantially tubular shape. The radiopaque marker 604 extends between a proximal end and a distal end and the length of the radiopaque marker 604 is less than the length of the recessed section 610. When the radiopaque marker 604 is secured to the mechanical waveguide 600 and for each point of the radiopaque marker 604 along the length thereof, the internal diameter of the radiopaque marker 604 is substantially equal to the diameter D3 of the recessed section The distal end of the radiopaque marker 604, i.e., the distal loop of the coil, abuts against the proximal portion 614 of the distal section 612. Since the length of the radiopaque marker 604 is less than that of the recessed section 610, the diameter of the radiopaque marker 604 at its proximal end is less than the diameter D1 of the proximal section 608.

Since the distal end of the radiopaque marker 604 abuts against the proximal portion 614 of the distal section 612 and the diameter of the proximal end of the radiopaque marker 604 is less than the maximal diameter of the recessed section 610, i.e., the diameter D1, the radiopaque marker 604 is secured to the mechanical waveguide 602 and cannot translate along the longitudinal axis of the mechanical waveguide 602. In one embodiment, the radiopaque marker 604 may rotate about the longitudinal axis of the mechanical waveguide 602 once secured thereto.

It should be understood that the dimensions of the radiopaque marker 604 may vary as long as its length is less than the length of the recessed section 610, its diameter at its proximal length is less than the maximal diameter of the recessed section, i.e., diameter D1, and its diameter at its distal end is less than the diameter D2 of the distal portion 616. For example, for each point along the length of the radiopaque marker 604, the diameter of the radiopaque marker 604 may be greater than the diameter of the recessed section 610 as long as the diameter of the proximal end of the radiopaque marker 604 is less than D1 and the diameter of the distal end of the radiopaque marker 604 is less than D2.

In one embodiment, the length of the protrusions such as protrusions 216, 218, 318, 402 and 403 is chosen so as to be short in comparison to the wavelength of the mechanical waves or pulses propagating through the mechanical waveguide or transmission member in order to minimize diffraction of the travelling mechanical waves or pulses and/or propagation losses. For example, the length of the protrusion along the longitudinal axis of the mechanical waveguide may be less than $1/10^{th}$ of the wavelength of the mechanical waves or pulses to be propagated in the mechanical waveguide.

The embodiments of the invention described above are intended to be exemplary only. The scope of the invention is therefore intended to be limited solely by the scope of the appended claims.

We claim:

1. A device for transmitting broadband pulsed mechanical waves, comprising:
    a mechanical waveguide having an elongated shape and extending between a proximal end and a distal end, the proximal end being operatively couplable to a mechanical wave pulse generator for propagating the broadband pulsed mechanical waves coupled at the proximal end up to the distal end of the mechanical waveguide, the mechanical waveguide having at least two protrusions projecting from an outer face thereof adjacent to the distal end; and
    a radiopaque marker secured to the mechanical waveguide adjacent to the distal end thereof a portion of the radiopaque marker being hollow and positioned over the mechanical waveguide between the two protrusions; and
    wherein the inner dimension of the portion of the radiopaque marker is greater than an outer dimension of a section of the mechanical waveguide between the two protrusions once the radiopaque marker is positioned between the two protrusions and deformed about the section of the mechanical waveguide so as to minimize leakage of the broadband pulsed mechanical waves.

2. The device of claim 1, wherein the mechanical waveguide comprising a recessed section between the two protrusions adjacent to the distal end and the radiopaque marker is positioned over at least a portion of the recessed section between the two protrusions.

3. The device of claim 2, wherein the mechanical waveguide comprises a proximal section and a distal section arranged on opposite sides of to the recessed section which is positioned between the two protrusions, the distal section comprising the distal end of the mechanical waveguide.

4. The device of claim 3, wherein the radiopaque marker extends between a first end and a second end, one or both ends abutting against one or both of the distal and proximal sections.

5. The device of claim 4, wherein the distal section comprises a first distal portion adjacent to the recessed section and having an increasing diameter, and a second distal portion having a constant diameter and extending up to the distal end of the elongated member, the second end of the radiopaque marker abutting against the first distal portion of the distal section.

6. The device of claim 5, wherein the proximal section comprises a first proximal portion adjacent to the recessed section and having a decreasing diameter, and a second proximal portion having a substantially constant diameter, the first end of the radiopaque marker abutting against the first proximal portion of the proximal section.

7. The device of claim 6, wherein the proximal section further comprises a third proximal portion having an increasing diameter, the second proximal portion being located between the first and third proximal portions.

8. The device of claim 2, wherein the radiopaque marker comprises a coil wound around the recessed section.

9. The device of claim 8, wherein the coil is a single layer coil.

10. The device of claim 8, wherein the coil is a multi-layer coil.

11. The device of claim 1, wherein the radiopaque marker is made of or coated with one of tungsten, platinum, gold, a gold alloy or a doped polymer.

12. The device of claim 1, wherein the mechanical waveguide is made of one of stainless steel, aluminum, aluminum alloy, titanium, titanium alloy, nitinol or fused quartz.

13. The device of claim 12, wherein the titanium alloy comprises one of Ti-6Al-4V, Ti-11.5Mo-6Zr-4.5Sn (Beta III titanium) or Ti-3Al-8V-6Cr-4Mo-4Zr (Beta C titanium).

14. The device of claim 1, wherein at least a portion of the elongated member is coated with one of a hydrophilic coating or a hydrophobic coating.

15. The device of claim 1, wherein at least a portion of the elongated member is coated with a friction-reducing coating.

16. An assembly for propagating broadband pulsed mechanical waves comprising:
- a mechanical waveguide comprising a first elongated structure extending along a first longitudinal axis between a proximal end and a distal end, the proximal end being operatively couplable to a mechanical wave pulse generator, the mechanical waveguide being provided with at least two protrusions projecting from an outer face thereof adjacent to the distal end, the two protrusions being spaced apart by a given distance along the first longitudinal axis; and
- a radiopaque marker comprising a second elongated structure made of a radiopaque material and extending along a second longitudinal axis, the second elongated structure being hollow so as to be positioned around the first elongated structure between the two protrusions and maintained between the two protrusions,
- wherein the inner dimension of the radiopaque marker is greater than an outer dimension of a section of the first elongated structure between the two protrusions once the radiopaque marker is positioned between the two protrusions and deformed about the section of the mechanical waveguide so as to minimize leakage of the broadband pulsed mechanical waves.

17. The assembly of claim 16, wherein the first elongated structure has a cylindrical shape and the second elongated structure has a tubular structure, an inner diameter of the second elongated structure being less than a traverse dimension of at least one of the two protrusions.

18. The assembly of claim 17, wherein the two protrusions extend along a portion of a circumference of the first elongated structure.

19. The assembly of claim 16, wherein the second elongated structure comprises a slot extending longitudinally from a proximal end thereof to a distal end thereof.

20. The assembly of claim 19, further comprising a tube insertable around the radiopaque marker.

21. A method for making a mechanical waveguide structure adapted to propagate broadband pulsed mechanical waves, the method comprising:
- providing a mechanical waveguide comprising a first elongated structure extending along a first longitudinal axis, the first elongated structure being operatively couplable to a mechanical wave pulse generator, the mechanical waveguide being provided with at least two protrusions projecting from an outer face of thereof, the two protrusions being spaced apart by a given distance along the first longitudinal axis;
- providing a radiopaque marker comprising a second elongated structure made of a radiopaque material, extending along a second longitudinal axis and having a length being one of less than and equal to the given distance, the second elongated structure being hollow so as to be positioned around the first elongated structure between the two protrusions for minimizing leakage of the broadband pulsed mechanical waves and being deformable so that an inner dimension thereof be reduced to maintain the second elongated structure between the two protrusions;
- positioning the second elongated structure around the first elongated structure between the two protrusions; and
- mechanically deforming the second elongated structure so that the inner dimension thereof be less than a traverse dimension of the two protrusions, thereby securing the radiopaque marker to the first elongated structure between the two protrusions, wherein the inner dimension of the radiopaque marker after said mechanically deforming is greater than an outer dimension of a section of the first elongated structure comprised between the two protrusions.

22. The method of claim 21, wherein said mechanically deforming comprises one of crimping or swaging the second elongated structure.

23. The method of claim 21, wherein the second elongated structure comprises a slot extending longitudinally from a proximal end thereof to a distal end thereof.

* * * * *